US012383462B1

(12) United States Patent
He et al.

(10) Patent No.: US 12,383,462 B1
(45) Date of Patent: Aug. 12, 2025

(54) FOOT REFLEX ZONES IDENTIFICATION METHOD, DEVICE, REHABILITATION ROBOT, AND STORAGE MEDIUM

(71) Applicant: JIANGHAN UNIVERSITY, Hubei (CN)

(72) Inventors: Qiang He, Hubei (CN); Lixin Yu, Hubei (CN); Hongxing Zhang, Hubei (CN); Qian Tu, Hubei (CN)

(73) Assignee: JIANGHAN UNIVERSITY, Wuhan (CN)

( * ) Notice: Subject to any disclaimer, the term of this patent is extended or adjusted under 35 U.S.C. 154(b) by 0 days.

(21) Appl. No.: 19/084,737

(22) Filed: Mar. 19, 2025

(30) Foreign Application Priority Data

Sep. 12, 2024 (CN) .......................... 202411278078.X

(51) Int. Cl.
*A61H 39/04* (2006.01)
*A61B 5/00* (2006.01)

(52) U.S. Cl.
CPC ........... *A61H 39/04* (2013.01); *A61B 5/0077* (2013.01); *A61H 2201/1659* (2013.01); *A61H 2205/125* (2013.01)

(58) Field of Classification Search
CPC ...................... A61H 2205/12; A61H 2205/125
See application file for complete search history.

(56) References Cited

FOREIGN PATENT DOCUMENTS

| CN | 106389107 A | 2/2017 |
|---|---|---|
| CN | 106446945 A | 2/2017 |
| CN | 112116016 A | 12/2020 |
| CN | 115634147 A | 1/2023 |
| CN | 116188769 A | 5/2023 |
| CN | 118365709 A | 7/2024 |
| KR | 20230141175 A | 10/2023 |
| WO | 2012126201 A1 | 9/2012 |
| WO | 2022062262 A1 | 3/2022 |

OTHER PUBLICATIONS

Notification to Grant Patent Right for Invention, Chinese Application No. 202411278078.X, mailed Nov. 23, 2024 (3 pages).
CNIPA, Office Action issued for Chinese Application No. 202411278078.X, mailed Oct. 31, 2024 (14 pages).
Quyen Manh Nguyen et al.; "Device to Detect Acupuncture Points in the Feet Soles for Massage Treatment", 8th International Conference on the Development of Biomedical Engineering in Vietnam, Full Text, issued Aug. 26, 2021.

*Primary Examiner* — Todd J Scherbel

(57) ABSTRACT

This invention provides a foot reflex zones identification method, device, rehabilitation robot, and storage medium. The method comprises the following steps: inputting a foot image into a multi-task deep learning network model, and obtaining foot part reflex zones and foot organ reflex zones; the foot part reflex zones include a head reflex zone, a neck reflex zone, a shoulder-back reflex zone, a chest reflex zone, an abdominal reflex zone, and a genital reflex zone; judging whether the foot organ reflex zones and the foot part reflex zones satisfy a theoretical position relationship, if the relationship is satisfied, determining the foot organ reflex zones as target foot organ reflex zones; wherein, the theoretical position relationship is that the foot organ reflex zones are sub-regions of each of the foot part reflex zones. This invention improves the accuracy of the identified target foot organ reflex zones.

6 Claims, 5 Drawing Sheets

FOOT REFLEX ZONES IDENTIFICATION METHOD, DEVICE, REHABILITATION ROBOT, AND STORAGE MEDIUM

FIELD OF THE DISCLOSURE

The invention relates to the fields of acupoint identification, particularly to a foot reflex zones identification method, device, rehabilitation robot, and storage medium.

BACKGROUND

The reflex zones on the sole of the foot, corresponding to various organs and body parts, include the reflex zones of the frontal sinus, nose, shoulder, thyroid, lung, stomach, kidney, liver, small intestine, thigh, gonad, buttocks, etc. Massaging the frontal sinus reflex zone can help alleviate concussion, sinusitis, and fever. Stimulating the nose reflex zone may assist in treating multiple sclerosis, poliomyelitis, or spinal cord tumors. Similarly, massaging the thyroid reflex zone can help clear the mind, soothe the nerves, and improve circulation, while the lung reflex zone can be beneficial in treating respiratory issues like tuberculosis, emphysema, and chest tightness. In clinical practice, specific reflex zones are strategically chosen based on the nature of different diseases. By employing massage techniques and scraping therapy to stimulate these foot reflex zones, the functionality of the corresponding visceral meridians, as well as the flow of qi and blood, can be effectively regulated. This holistic approach ultimately aims to achieve therapeutic effects for various ailments.

Traditionally, identifying foot reflex zones relies on the accumulated experience and techniques of practitioners of traditional Chinese medicine. This method, however, is highly subjective and requires significant expertise, resulting in low accuracy and efficiency. While modern approaches, such as image recognition algorithms based on computer vision (e.g., YOLOv8), have improved identification to some extent, these methods still face challenges with verifying the accuracy of the identified reflex zones. When the foot reflex zones are inaccurately identified, it can significantly impact the effectiveness of the treatment.

Therefore, there is an urgent need to develop a foot reflex zones identification method, device, rehabilitation robot, and storage medium that can validate the results of the identification algorithm, ensuring the accuracy of the reflex zones identified for treatment purposes.

SUMMARY

The invention aims to address the problem of unverified identification results by providing a foot reflex zones identification method, device, rehabilitation robot, and storage medium that also ensures the accuracy of the identification through validation.

In one aspect, the present invention provides a foot reflex zones identification method, which comprises:
  inputting a foot image into a multi-task deep learning network model to obtain both foot part reflex zones and foot organ reflex zones; the foot part reflex zones include the head, neck, shoulder-back, chest, abdominal, and genital reflex zones;
  judging whether the foot organ reflex zones and the foot part reflex zones satisfy a theoretical position relationship; if the relationship is satisfied, the foot organ reflex zones are confirmed as the target reflex zones;
  wherein the theoretical position relationship is that the foot organ reflex zones are sub-regions of each of the foot part reflex zones.

In some possible implementation methods, the step of judging whether the foot organ reflex zones and the foot part reflex zones satisfy the theoretical position relationship, comprises:
  determining a first region coordinate range of each of the foot part reflex zone in a preset coordinate system and a second region coordinate range of each of the foot organ reflex zone in the preset coordinate system;
  determining an actual position relationship between the foot organ reflex zones and the foot part reflex zones based on the first region coordinate range and the second region coordinate range;
  when the actual position relationship is the same as the theoretical position relationship, the foot organ reflex zones and the foot part reflex zones satisfy the theoretical position relationship.

In some possible implementation methods, the foot organ reflex zones include a first group of organ reflex sub-zones corresponding to the head reflex zone, a second group of organ reflex sub-zones corresponding to the neck reflex zone, a third group of organ reflex sub-zones corresponding to the shoulder-back reflex zone, a fourth group of organ reflex sub-zones corresponding to the chest reflex zone, a fifth group of organ reflex sub-zones corresponding to the abdominal reflex zone, and a sixth group of organ reflex sub-zones corresponding to the genital reflex zone;
  then, the step of judging whether the foot organ reflex zones and the foot part reflex zones satisfy the theoretical position relationship, comprises:
  judging whether the first group of organ reflex sub-zones and the head reflex zone, the second group of organ reflex sub-zones and the neck reflex zone, the third group of organ reflex sub-zones and the shoulder-back reflex zone, the fourth group of organ reflex sub-zones and the chest reflex zone, the fifth group of organ reflex sub-zones and the abdominal reflex zone, and the sixth group of organ reflex sub-zones and the genital reflex zone satisfy the theoretical position relationship.

In some possible implementation methods, before the step of judging whether the foot organ reflex zones and the foot part reflex zones satisfy the theoretical position relationship, the method further comprises:
  obtaining a theoretical part orientation relationship and an actual part orientation relationship between the foot part reflex zones;
  judging whether the actual part orientation relationship satisfies the theoretical part orientation relationship;
  then, the step of judging whether the foot organ reflex zones and the foot part reflex zones satisfy the theoretical position relationship specifically is:
  when the actual part orientation relationship satisfies the theoretical part orientation relationship, judging whether the foot organ reflex zones and the foot part reflex zones satisfy the theoretical position relationship.

In some possible implementation methods, before the step of judging whether the foot organ reflex zones and the foot part reflex zones satisfy the theoretical position relationship, the method further comprises:
  determining a first sub-zone orientation relationship of the first group of organ reflex sub-zones, a second sub-zone orientation relationship of the second group of organ reflex sub-zones, a third sub-zone orientation relationship of the third group of organ reflex sub-zones, a fourth sub-zone orientation relationship of the fourth group of organ reflex sub-zones, a fifth sub-zone orientation relationship of the fifth group of organ reflex sub-zones, and a sixth sub-zone orientation relationship of the sixth group of organ reflex sub-zones;

judging whether the first sub-zone orientation relationship, the second sub-zone orientation relationship, the third sub-zone orientation relationship, the fourth sub-zone orientation relationship, the fifth sub-zone orientation relationship, and the sixth sub-zone orientation relationship satisfy a theoretical organ orientation relationship;

then, the step of judging whether the foot organ reflex zones and the foot part reflex zones satisfy the theoretical position relationship specifically is:

when the first sub-zone orientation relationship, the second sub-zone orientation relationship, the third sub-zone orientation relationship, the fourth sub-zone orientation relationship, the fifth sub-zone orientation relationship, and the sixth sub-zone orientation relationship satisfy the theoretical organ orientation relationship, judging whether the foot organ reflex zones and the foot part reflex zones satisfy the theoretical position relationship.

In some possible implementation methods, the first group of organ reflex sub-zones includes a brain reflex sub-zone, a nose reflex sub-zone, an oral cavity reflex sub-zone, an eye reflex sub-zone, an ear reflex sub-zone, and a frontal sinus reflex sub-zone; the second group of organ reflex sub-zones includes an esophagus-trachea reflex sub-zone, a neck reflex sub-zone, a thyroid reflex sub-zone, and a parathyroid reflex sub-zone; the third group of organ reflex sub-zones includes a trapezius muscle reflex sub-zone and a shoulder reflex sub-zone; the fourth group of organ reflex sub-zones includes a bronchus reflex sub-zone and a lung reflex sub-zone; the fifth group of organ reflex sub-zones includes a liver reflex sub-zone, a kidney reflex sub-zone, a stomach reflex sub-zone, a duodenum reflex sub-zone, a transverse colon reflex sub-zone, an ascending colon reflex sub-zone, a small intestine reflex sub-zone, and a bladder reflex sub-zone; the sixth group of organ reflex sub-zones includes a pelvic region reflex sub-zone, a buttocks reflex sub-zone, and a gonad reflex sub-zone.

In some possible implementation methods, the multi-task deep learning network model includes a shared backbone sub-model, and a parallel organ reflex zone detection head and a part reflex zone detection head. Then, the step of inputting an image of a foot to be identified into the multi-task deep learning network model to obtain foot part reflex zones and foot organ reflex zones comprises:

obtaining shared image features based on the shared backbone sub-model, the shared backbone sub-model used for feature extraction of the foot image;

obtaining the foot organ reflex zones based on the organ reflex zone detection head, the organ reflex zone detection head used for key point detection of the shared image features;

obtaining the foot part reflex zones based on the part reflex zone detection head, the part reflex zone detection head used for semantic segmentation of the shared image features.

In another aspect, the present invention also provides a foot reflex zones identification device, which comprises:

foot reflex zone initial identification unit, configured to input a foot image into a multi-task deep learning network model to obtain foot part reflex zones and foot organ reflex zones; the foot part reflex zones include a head reflex zone, a neck reflex zone, a shoulder-back reflex zone, a chest reflex zone, an abdominal reflex zone, and a genital reflex zone;

foot organ reflex zone determination unit, configured to judge whether the foot organ reflex zones and the foot part reflex zones satisfy a theoretical position relationship, and if the relationship is satisfied, determining the foot organ reflex zones as target foot organ reflex zones; wherein the theoretical position relationship is that the foot organ reflex zones are sub-regions of each of the foot part reflex zones.

In another aspect, the present invention also provides a rehabilitation robot, including a memory and a processor, wherein the memory is configured to store a program;

the processor is coupled to the memory and is configured to execute the program to implement the foot reflex zones identification method in any of the aforementioned possible implementation methods.

In another aspect, the present invention also provides a computer-readable storage medium. A program or instructions are stored on the computer-readable storage medium. When the program or instructions are executed by a processor, the foot reflex zones identification method described in any of the aforementioned possible implementation methods is implemented.

The beneficial effects of adopting the aforementioned embodiments are as follows: The foot reflex zones identification method provided by the present invention involves inputting an image of a foot to be identified into a multi-task deep learning network model to obtain foot part reflex zones and foot organ reflex zones. The accuracy of the foot organ reflex zones can be verified based on the foot part reflex zones, that is, the foot part reflex zones serve as the verification conditions for the foot organ reflex zones. When the foot organ reflex zones and the foot part reflex zones satisfy the theoretical position relationship, the foot organ reflex zones are determined as the target foot organ reflex zones, which improves the accuracy of the identified target foot organ reflex zones.

Further, since the foot organ reflex zones are sub-regions of each of the foot part reflex zones, that is, the foot part reflex zones have a larger area than the foot organ reflex zones, the identification accuracy of the foot part reflex zones is higher. Verifying the foot organ reflex zones based on the foot part reflex zones with higher identification accuracy can further improve the accuracy of the foot organ reflex zones.

Furthermore, the multi-task deep learning network model in the present invention can obtain the foot part reflex zones through semantic segmentation and the foot organ reflex zones through key point detection. Using one network model to implement different tasks simplifies the model structure, saves computing resources, and thus improves the identification efficiency of the foot reflex zones.

BRIEF DESCRIPTION OF THE FIGURES

To describe the technical solutions in embodiments of the present invention more clearly, the following briefly introduces the accompanying drawings for describing the embodiments. Apparently, the accompanying drawings in the following description show merely some embodiments of the present invention, and those skilled in the art may still derive other accompanying drawings from these accompanying drawings without making creative efforts.

DETAILED DESCRIPTION

The following clearly and completely describes the technical solutions in the embodiments of the present invention with reference to the accompanying drawings in the embodiments of the present invention. Apparently, the embodiments described are merely a part rather than all of the embodiments of the present invention. Based on the embodiments in the present invention, all other embodiments obtained by those skilled in the art without making creative efforts shall fall within the scope of protection of the present invention.

It should be understood that the schematic drawings are not drawn in proportion to physical objects. Flowcharts used in the present invention show operations implemented according to some embodiment of the present invention. It should be understood that the operations of the flowcharts can be implemented out of order, and the steps without a logical contextual relationship may be implemented in reverse order or implemented at the same time. In addition, under the guidance of the content of the present invention, those skilled in the art can add one or more other operations to each flowchart, and can also remove one or more operations from each flowchart. Some of block diagrams shown in the accompanying drawings are functional entities and do not necessarily have to correspond to physically or logically separate entities. These functional entities may be implemented in software, or implemented in one or more hardware modules or integrated circuits, or implemented in different network and/or processor systems and/or microcontroller systems.

The description of "first", "second" involved in the embodiment of the present invention are for descriptive purposes only, and cannot be understood to indicate or imply relative importance or implicitly indicate the quantity of indicated technical features. Therefore, the technical features defined by "first" and "second" may explicitly or implicitly include at least one such feature.

The reference to "Embodiment" herein means that a particular feature, structure, or characteristic described with reference to the embodiment may be included in at least one embodiment of the present invention. The appearances of the phrases in various places in the specification may not refer to the same embodiment, or to an independent or alternative embodiment that is mutually exclusive of other embodiments. Those skilled in the art explicitly and implicitly understand that the embodiment described herein may be combined with other embodiments.

The present invention provides foot reflex zones identification method, device, rehabilitation robot, and storage medium, which are described separately.

Figure 1:
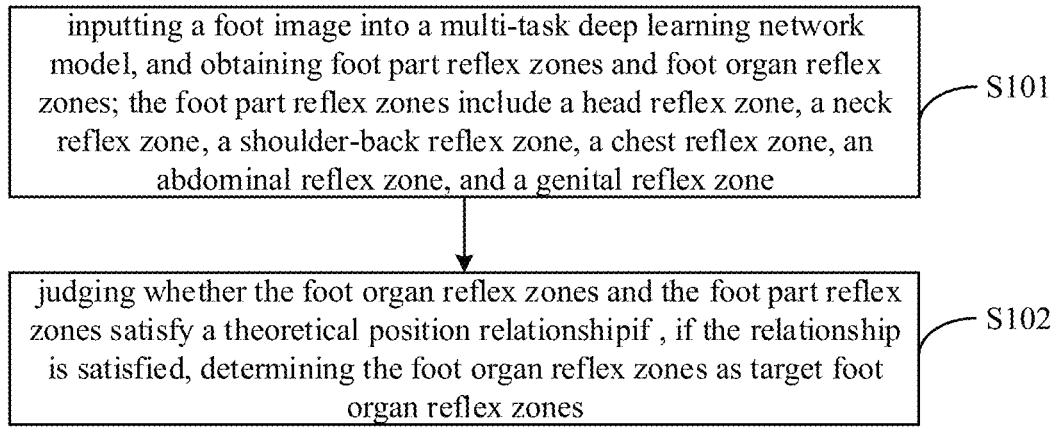
FIG. 1 is a flowchart of the foot reflex zones identification method provided by the present invention.
Figure 2:
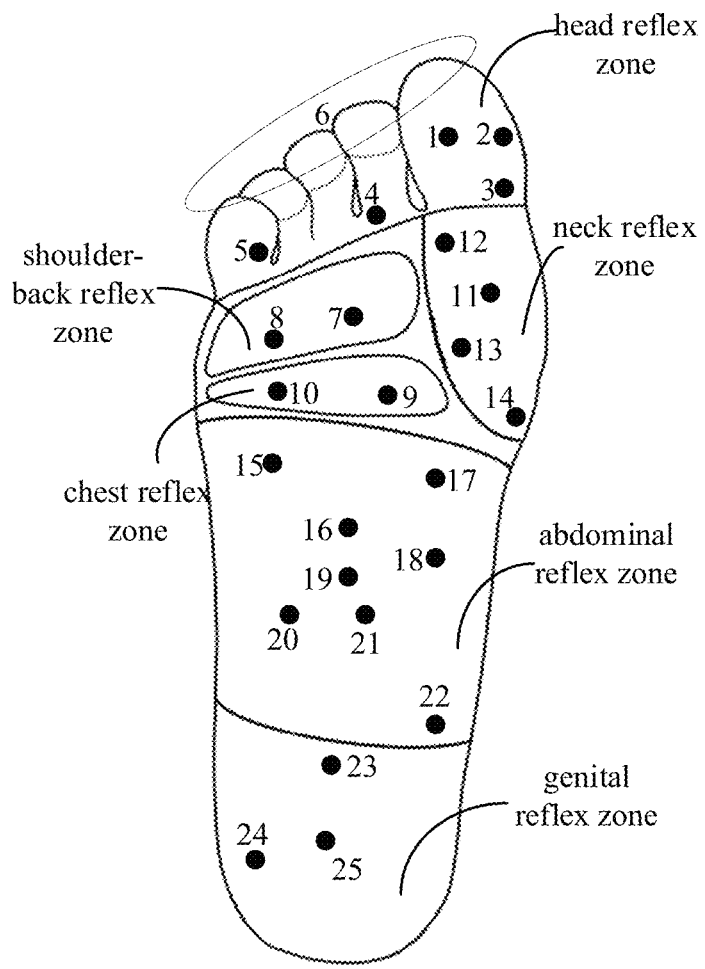
FIG. 2 is a schematic diagram of the foot part reflex zones and the foot organ reflex zones provided by the present invention.

FIG. 1 is a flowchart of the foot reflex zones identification method, FIG. 2 is a schematic diagram of the foot part reflex zones and the foot organ reflex zones. As shown in FIG. 1 and FIG. 2, the foot reflex zones identification method comprises:

S101, inputting a foot image into a multi-task deep learning network model, and obtaining foot part reflex zones and foot organ reflex zones; the foot part reflex zones include a head reflex zone, a neck reflex zone, a shoulder-back reflex zone, a chest reflex zone, an abdominal reflex zone, and a genital reflex zone;

S102, judging whether the foot organ reflex zones and the foot part reflex zones satisfy a theoretical position relationship, if the relationship is satisfied, determining the foot organ reflex zones as target foot organ reflex zones;

wherein, the theoretical position relationship is that the foot organ reflex zones are sub-regions of each of the foot part reflex zones.

It should be understood that before S101, the multi-task deep learning network model needs to be trained, tested, and verified according to sample data to obtain an optimized multi-task deep learning network model capable of identifying foot images.

Specifically, the process of producing sample data involves using a camera to collect a plantar image data set. During the collection, images from different angles are collected to ensure that the multi-task deep learning network model can accurately detect and identify foot part reflex zones and foot organ reflex zones in foot images taken from various angles. Additionally, to enhance accuracy, it is required that the sole of the foot is free from foreign objects and occlusions, thereby reducing interference and improving the accuracy and stability of identification.

It should also be understood that if the foot organ reflex zones and the foot part reflex zones do not satisfy the theoretical position relationship, S101 will be re-executed, or the multi-task deep learning network model will be re-trained. The foot reflex zones identification method described in the embodiments of the present invention can be implemented in any device that identifies foot acupoints, such as acupuncture robots or massage robots. Specifically, the foot reflex zones identification method is stored in these devices as a compiled program. When the device is started, the program is called, and the foot reflex zones identification method is executed.

Compared with the prior art, the foot reflex zones identification method provided by the present invention is designed to input an image of a foot to be identified into a multi-task deep learning network model to obtain foot part reflex zones and foot organ reflex zones. The accuracy of the foot organ reflex zones is verified based on the foot part reflex zones, which serve as the verification conditions. When the foot organ reflex zones and the foot part reflex zones satisfy the theoretical position relationship, the foot organ reflex zones are determined as the target foot organ reflex zones, thereby enhancing the accuracy of the identified target foot organ reflex zones.

Further, since the organ reflex zones are sub-regions of the foot part reflex zones, the identification accuracy of the foot part reflex zones is inherently higher. Verifying the foot organ reflex zones based on the foot part reflex zones further enhances the accuracy of the foot organ reflex zones.

Furthermore, the multi-task deep learning network model in the present invention can obtain the foot part reflex zones through semantic segmentation and the foot organ reflex zones through key point detection. Using one network model to implement multiple different tasks simplifies the model structure, saves computing resources, and thereby improving the identification efficiency of the foot reflex zones.

Figure 3:
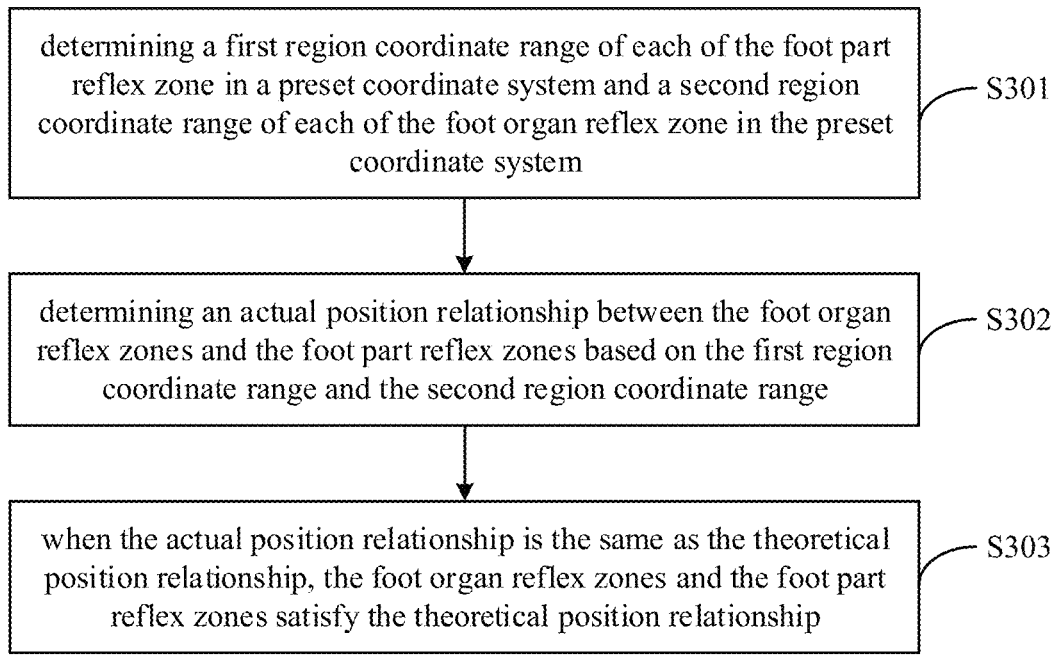
FIG. 3 is a flowchart of S102 in FIG. 1 of the present invention.

In some embodiments of the present invention, as shown in FIG. 3, S102 comprises:
- S301, determining a first region coordinate range of each of the foot part reflex zone in a preset coordinate system and a second region coordinate range of each of the foot organ reflex zone in the preset coordinate system;
- S302, determining an actual position relationship between the foot organ reflex zones and the foot part reflex zones based on the first region coordinate range and the second region coordinate range;
- S303, when the actual position relationship matches the theoretical position relationship, the foot organ reflex zones and the foot part reflex zones satisfy the theoretical position relationship.

The determination process of the first region coordinate range involves determining the boundary line of the first region and multiple pixel points on the boundary line. The coordinates of each pixel point are then obtained in the preset coordinate system, and the first region coordinate range is determined based on these coordinates.

The determination process of the second region coordinate range is the same as that of the first region coordinate range and is omitted for brevity.

Since the foot organ reflex zones include a first group of organ reflex sub-zones corresponding to the head reflex zone, a second group of organ reflex sub-zones corresponding to the neck reflex zone, a third group of organ reflex sub-zones corresponding to the shoulder-back reflex zone, a fourth group of organ reflex sub-zones corresponding to the chest reflex zone, a fifth group of organ reflex sub-zones corresponding to the abdominal reflex zone, and a sixth group of organ reflex sub-zones corresponding to the genital reflex zone.

If only considering that the foot organ reflex zones are sub-regions of the foot part reflex zones, a situation may occur where the first group of organ reflex sub-zones is located in the shoulder-back reflex zone and is deemed to satisfy the theoretical position relationship. Obviously, the identification result of the first group of organ reflex sub-zones in this case would be incorrect. To avoid mis-identification in similar situations, in some embodiments of the present invention, S102 specifically includes:
- judging whether the first group of organ reflex sub-zones and the head reflex zone, the second group of organ reflex sub-zones and the neck reflex zone, the third group of organ reflex sub-zones and the shoulder-back reflex zone, the fourth group of organ reflex sub-zones and the chest reflex zone, the fifth group of organ reflex sub-zones and the abdominal reflex zone, and the sixth group of organ reflex sub-zones and the genital reflex zone satisfy the theoretical position relationship.

Specifically, the theoretical position relationship requires that the first group of organ reflex sub-zones is located within the head reflex zone, the second group of organ reflex sub-zones is located within the neck reflex zone, the third group of organ reflex sub-zones is located within the shoulder-back reflex zone, the fourth group of organ reflex sub-zones is located within the chest reflex zone, the fifth group of organ reflex sub-zones is located within the abdominal reflex zone, and the sixth group of organ reflex sub-zones is located within the genital reflex zone.

The embodiments of the present invention ensure that different groups of organ reflex sub-zones are located within their corresponding foot part reflex zones by setting a additional theoretical position relationship, thereby further enhancing the accuracy of identifying the foot organ reflex zones.

In the specific embodiments of the present invention, as shown in FIG. 2, the first group of organ reflex sub-zones includes a brain reflex sub-zone 1, a nose reflex sub-zone 2, an oral cavity reflex sub-zone 3, an eye reflex sub-zone 4, an ear reflex sub-zone 5, and a frontal sinus reflex sub-zone 6; the second group of organ reflex sub-zones includes an esophagus-trachea reflex sub-zone 11, a neck reflex sub-zone 12, a thyroid gland reflex sub-zone 13, and a parathyroid gland reflex sub-zone 14; the third group of organ reflex sub-zones includes a trapezius muscle reflex sub-zone 7 and a shoulder reflex sub-zone 8; the fourth group of organ reflex sub-zones includes a bronchus reflex sub-zone 9 and a lung reflex sub-zone 10; the fifth group of organ reflex sub-zones includes a liver reflex sub-zone 15, a kidney reflex sub-zone 16, a stomach reflex sub-zone 17, a duodenum reflex sub-zone 18, a transverse colon reflex sub-zone 19, an ascending colon reflex sub-zone 20, a small intestine reflex sub-zone 21, and a bladder reflex sub-zone 22; the sixth group of organ reflex sub-zones includes a pelvic region reflex sub-zone 23, a hip reflex sub-zone 24, and a gonad reflex sub-zone 25.

Figure 4:
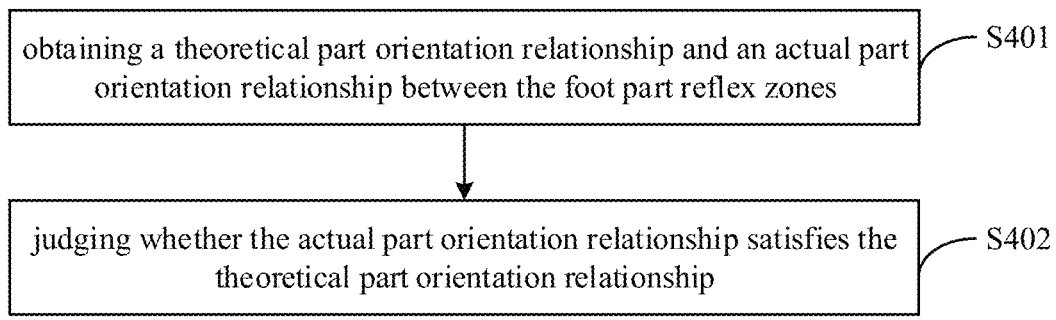
FIG. 4 is a flowchart of verifying the foot part reflex zones provided by the present invention.

As can be seen from FIG. 2, the foot part reflex zones have different position relationship. For example, the head reflex zone is located above the shoulder-back reflex zone, and the shoulder-back reflex zone and the chest reflex zone are located on the left side of the neck reflex zone. To further ensure the accuracy of the identified foot part reflex zones, in some embodiments of the present invention, as shown in FIG. 4, before S102, the method further comprises:
- S401, obtaining a theoretical part orientation relationship and an actual part orientation relationship between the foot part reflex zones;
- S402, judging whether the actual part orientation relationship satisfies the theoretical part orientation relationship.

The embodiments of the present invention can ensure the accuracy of the identified foot part reflex zones by verifying the foot part reflex zones based on the theoretical part position relationship.

Specifically, the theoretical part position relationship is that the head reflex zone is located above the shoulder-back reflex zone and the neck reflex zone, the shoulder-back reflex zone and the chest reflex zone are located on the left side of the neck reflex zone, the abdominal reflex zone is located below the chest reflex zone, and the genital reflex zone is located below the abdominal reflex zone.

Here, "above" and "below" refer to the direction with the toes of the foot as the upper direction and the heel as the lower direction.

Then S102 is:
- when the actual part orientation relationship satisfies the theoretical part orientation relationship, judging whether the foot organ reflex zones and the foot part reflex zones satisfy the theoretical position relationship.

Figure 5:
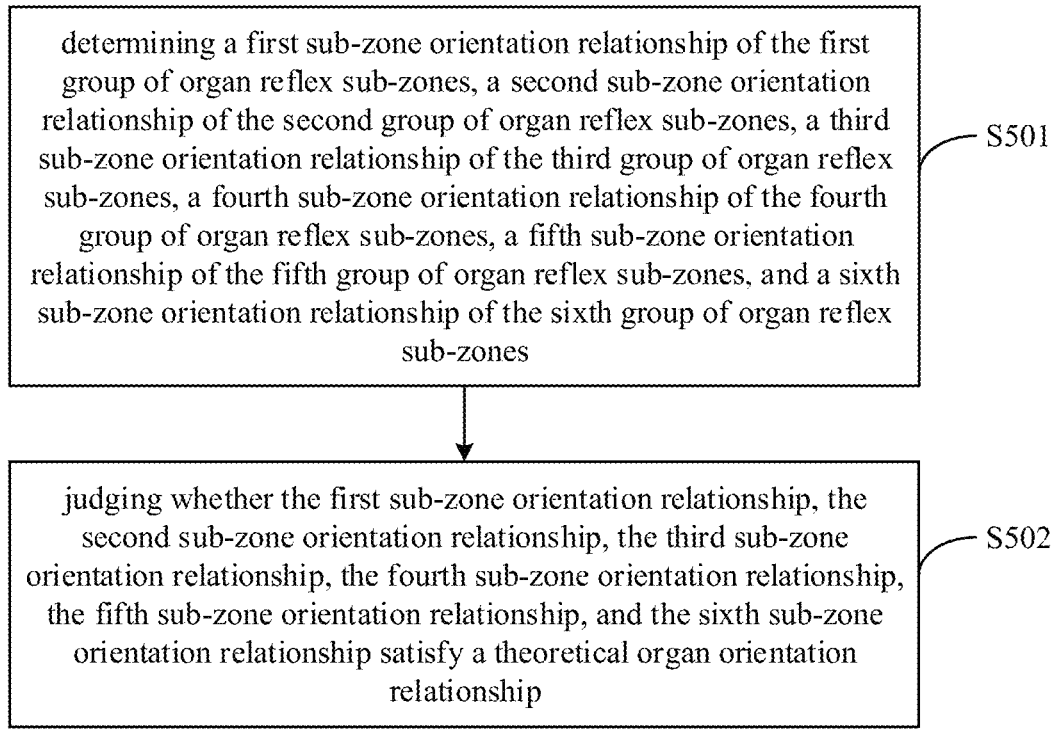
FIG. 5 is a flowchart of verifying the foot organ reflex zones provided by the present invention.

Furthermore, as can be seen from FIG. 2, different groups of organ reflex sub-zones also have different position relationship. For example, the transverse colon reflex sub-zone is located above the small intestine reflex sub-zone. To further improve the accuracy of identifying foot organ reflex zones, in some embodiments of the present invention, as shown in FIG. 5, before S102, the method further comprises:

S501, determining a first sub-zone orientation relationship of the first group of organ reflex sub-zones, a second sub-zone orientation relationship of the second group of organ reflex sub-zones, a third sub-zone orientation relationship of the third group of organ reflex sub-zones, a fourth sub-zone orientation relationship of the fourth group of organ reflex sub-zones, a fifth sub-zone orientation relationship of the fifth group of organ reflex sub-zones, and a sixth sub-zone orientation relationship of the sixth group of organ reflex sub-zones;

S502, judging whether the first sub-zone orientation relationship, the second sub-zone orientation relationship, the third sub-zone orientation relationship, the fourth sub-zone orientation relationship, the fifth sub-zone orientation relationship, and the sixth sub-zone orientation relationship satisfy a theoretical organ orientation relationship.

Then, S102 is:

when the first sub-zone orientation relationship, the second sub-zone orientation relationship, the third sub-zone orientation relationship, the fourth sub-zone orientation relationship, the fifth sub-zone orientation relationship, and the sixth sub-zone orientation relationship satisfy the theoretical organ orientation relationship, judging whether the foot organ reflex zones and the foot part reflex zones satisfy the theoretical position relationship.

The embodiments of the present invention can ensure the accuracy of the identified organ reflex sub-zones of each group by verifying the identification accuracy of the identified organ reflex sub-zones based on the theoretical organ position relationship, thereby improving the accuracy of the finally obtained target foot reflex zones.

Specifically, the theoretical position relationship is as follows: for the first group of organ reflex sub-zones, the position relationship from left to right is the ear reflex sub-zone, the eye reflex sub-zone, the brain reflex sub-zone, the left side of the nose reflex sub-zone. The oral cavity reflex sub-zone is located below the nose reflex sub-zone, and the frontal sinus reflex sub-zone is located above the left side of the ear reflex sub-zone, the eye reflex sub-zone, the brain reflex sub-zone, and the nose reflex sub-zone. For the second group of organ reflex sub-zones, the position relationship from top to bottom is the neck reflex sub-zone, the esophagus-trachea reflex sub-zone, the thyroid gland reflex sub-zone, and the parathyroid gland reflex sub-zone. For the third group of organ reflex sub-zones, the trapezius muscle reflex sub-zone is located on the right side of the shoulder reflex sub-zone. For the fourth group of organ reflex sub-zones, the bronchus reflex sub-zone is located on the right side of the lung reflex sub-zone. For the fifth group of organ reflex sub-zones, the kidney reflex sub-zone is located below the mid-point of the line connecting the liver reflex sub-zone and the stomach reflex sub-zone. The duodenum reflex sub-zone is located below the stomach reflex sub-zone, the transverse colon reflex sub-zone is located below the kidney reflex sub-zone, the small intestine reflex sub-zone is located below the transverse colon reflex sub-zone, the ascending colon reflex sub-zone is located on the left side of the small intestine reflex sub-zone, and the bladder reflex sub-zone is located below the duodenum reflex sub-zone and on the right side of the small intestine reflex sub-zone. For the sixth group of organ reflex sub-zones, the gonad reflex sub-zone is located below the pelvic region reflex sub-zone, and the hip reflex sub-zone is located on the left side of the gonad reflex sub-zone.

Figure 6:
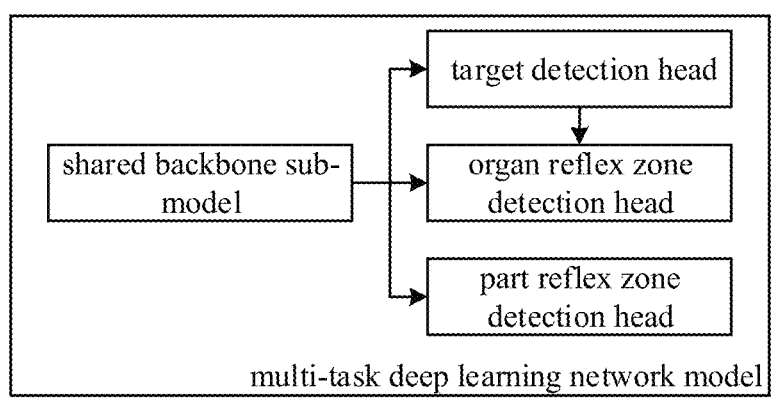
FIG. 6 is a schematic structural diagram of the multi-task deep learning network model provided by the present invention.
Figure 7:
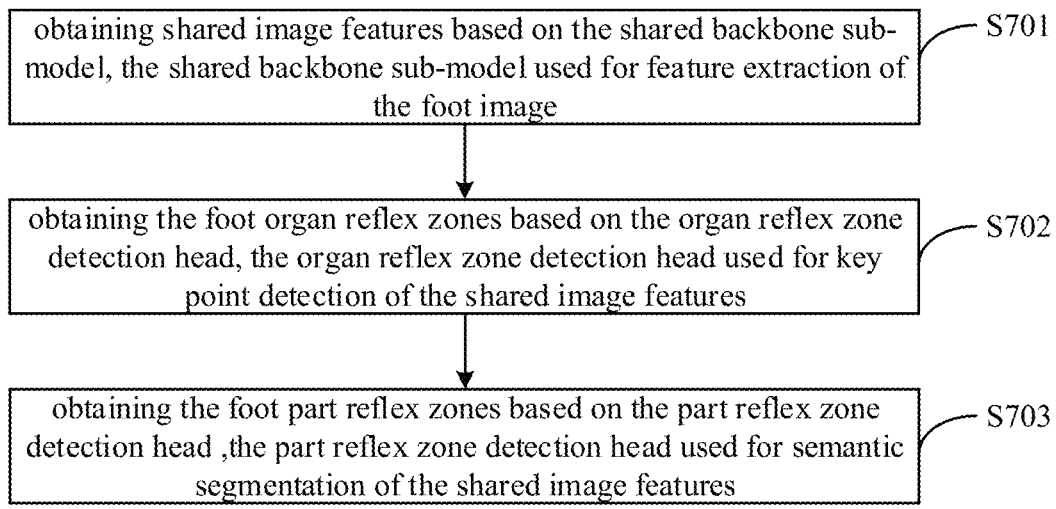
FIG. 7 is a flowchart of S101 in FIG. 1 of the present invention.

In some embodiments of the present invention, as shown in FIG. 6, the multi-task deep learning network model includes a shared backbone sub-model, and a parallel organ reflex zone detection head and a part reflex zone detection head. Then, as shown in FIG. 7, S101 comprises:

S701, obtaining shared image features based on the shared backbone sub-model, the shared backbone sub-model used for feature extraction of the foot image;

S702, obtaining the foot organ reflex zones based on the organ reflex zone detection head, the organ reflex zone detection head used for key point detection of the shared image features;

S703, obtaining the foot part reflex zones based on the part reflex zone detection head, the part reflex zone detection head used for semantic segmentationof the shared image features.

The embodiments of the present invention simplify the model structure and improve the identification efficiency of foot part reflex zones and foot organ reflex zones by setting the organ reflex zone detection head and the part reflex zone detection head of the multi-task deep learning network model to share the shared backbone sub-model, so that the shared image features determined by the shared backbone sub-model can be used as the input of both the organ reflex zone detection head and the part reflex zone detection head at the same time.

It should be noted that when the foot image contains other objects in addition to the foot, to ensure the accuracy of identifying foot part reflex zones and foot organ reflex zones, as shown in FIG. 6, the multi-task deep learning network model also includes a target detection head. The target detection head performs target detection on the shared image features to obtain the foot contour. Then, the part reflex zone detection head determines the foot part reflex zones based on the shared image features and the foot contour, and the organ reflex zone detection head determines the foot organ reflex zones based on the shared image features and the foot contour.

In the specific embodiments of the present invention, the multi-task deep learning network model is CenterNet, which can directly use the graph generated by the feature map and does not need to discretize the bounding-box detection using default bounding boxes.

Wherein, the part reflex zone detection head is implemented by a fully-convolutional network, and the organ reflex zone detection head is implemented by regressing the offset.

Figure 8:
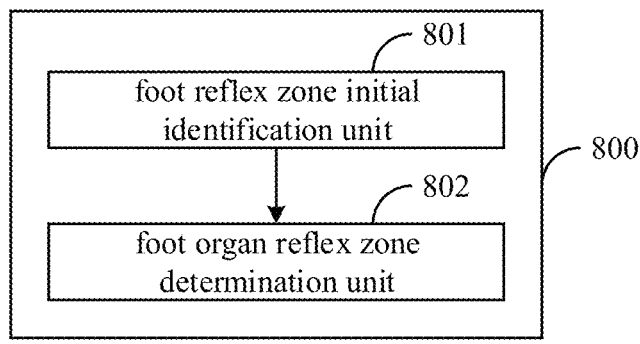
FIG. 8 is a schematic structural diagram of the foot reflex zones identification device provided by the present invention.

Corresponding to the foot reflex zones identification method, the present invention also provides a foot reflex zones identification device. As shown in FIG. 8, the foot reflex zones identification device 800 includes:

foot reflex zone initial identification unit 801, configured to input a foot image into a multi-task deep learning network model to obtain foot part reflex zones and foot organ reflex zones; the foot part reflex zones include a head reflex zone, a neck reflex zone, a shoulder-back reflex zone, a chest reflex zone, an abdominal reflex zone, and a genital reflex zone;

foot organ reflex zone determination unit 802, configured to judge whether the foot organ reflex zones and the foot part reflex zones satisfy a theoretical position relationship, when they satisfy the relationship, determining the foot organ reflex zones as target foot organ reflex zones;

Here, the theoretical position relationship is that the foot organ reflex zones are sub-regions of each foot part reflex zone.

The foot reflex zones identification device 800 provided by the above mentioned embodiments can implement the technical solutions described in the embodiments of the foot reflex zones identification method. The specific implementation principles of the above mentioned modules or units can be referred to the corresponding content in the embodiments of the foot reflex zones identification method, and will not be repeated here.

Figure 9:
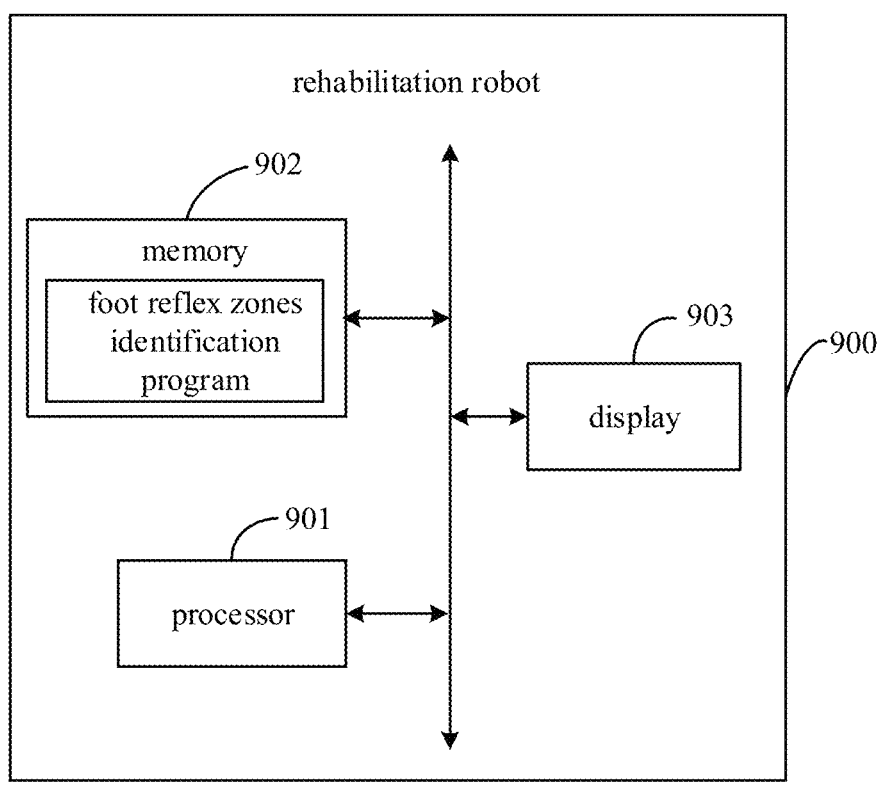
FIG. 9 is a schematic structural diagram of the rehabilitation robot provided by the present invention.

As shown in FIG. 9, the present invention also provides a rehabilitation robot 900. The rehabilitation robot 900 includes a processor 901, a memory 902, and a display 903. FOG. 9 only shows some components of the rehabilitation robot 900. It should be understood that it is not required to implement all the shown components, and more or fewer components can be implemented alternatively.

The memory 902 can be an internal storage unit of the rehabilitation robot 900 in some embodiments, such as a hard disk or memory of the rehabilitation robot 900. In other embodiments, the memory 902 can also be an external storage device of the rehabilitation robot 900, such as a plug-in hard disk, a Smart Media Card (SMC), a Secure Digital (SD) card, a Flash Card, etc. equipped on the rehabilitation robot 900.

Further, the memory 902 can include both the internal storage unit and the external storage device of the rehabilitation robot 900. The memory 902 is used to store the application software installed on the rehabilitation robot 900 and various types of data.

The processor 901 can be a Central Processing Unit (CPU), a micro processor, or other data processing chips in some embodiments. It is used to run the program code stored in the memory 902 or process data, such as the foot reflex zones identification method of the present invention.

In some embodiments, the display 903 can be an LED display, a liquid crystal display, a touch type liquid crystal display, an OLED (Organic Light-Emitting Diode) touch device, etc. The display 903 is used to display the information of the rehabilitation robot 900 and a visual user interface. The components 901-903 of the rehabilitation robot 900 communicate with each other through the system bus.

In some embodiments of the present invention, when the processor 901 executes the foot reflex zones identification program in the memory 902, the following steps can be implemented:

inputting a foot image into a multi-task deep learning network model, and obtaining foot part reflex zones and foot organ reflex zones; the foot part reflex zones include a head reflex zone, a neck reflex zone, a shoulder-back reflex zone, a chest reflex zone, an abdominal reflex zone, and a genital reflex zone;

judging whether the foot organ reflex zones and the foot part reflex zones satisfy a theoretical position relationship, when they satisfy the relationship, determining the foot organ reflex zones as target foot organ reflex zones;

wherein, the theoretical position relationship is that the foot organ reflex zones are sub-regions of each of the foot part reflex zones.

It should be understood that when the processor 901 executes the foot reflex zones identification program in the memory 902, in addition to the above mentioned functions, it can also implement other functions. For specific details, please refer to the descriptions of the relevant method embodiments above.

Correspondingly, the embodiments of the present invention also provide a computer-readable storage medium. The computer-readable storage medium is used to store programs or instructions that can be read by a computer. When the programs or instructions are executed by a processor, they can implement the steps or functions of the foot reflex zones identification method provided by the above mentioned method embodiments.

It is understood by those skilled in the art that all or part of the process to implement the above implementations may be accomplished by instructs the relevant hardware (e.g. processor, controller, etc.) through a computer program that may be stored in a computer readable storage medium. Among them, the computer readable storage medium is disk, optical disc, read-only storage memory or random storage memory.

The above foot reflex zones identification method, device, rehabilitation robot, and storage medium provided by the invention are introduced in detail. The principle and implementation mode of the invention are described in this paper with specific examples. The above implementation is only used to help understand the method and its core idea of the invention. At the same time, for the technical personnel in the field, according to the idea of the invention, there will be changes in the specific mode of implementation and scope of application, in summary, the content of this specification should not be understood as a limitation of the invention.

What is claimed is:

1. A foot reflex zones identification method, comprises:
inputting a foot image into a multi-task deep learning network model, and obtaining foot part reflex zones and foot organ reflex zones; the foot part reflex zones include a head reflex zone, a neck reflex zone, a shoulder-back reflex zone, a chest reflex zone, an abdominal reflex zone, and a genital reflex zone;
judging whether the foot organ reflex zones and the foot part reflex zones satisfy a theoretical position relationship, when they satisfy the relationship, determining the foot organ reflex zones as target foot organ reflex zones;
wherein, the theoretical position relationship is that the foot organ reflex zones are sub-regions of each of the foot part reflex zones;
the foot organ reflex zones include a first group of organ reflex sub-zones corresponding to the head reflex zone, a second group of organ reflex sub-zones corresponding to the neck reflex zone, a third group of organ reflex sub-zones corresponding to the shoulder-back reflex zone, a fourth group of organ reflex sub-zones corresponding to the chest reflex zone, a fifth group of organ reflex sub-zones corresponding to the abdominal reflex zone, and a sixth group of organ reflex sub-zones corresponding to the genital reflex zone;
before judging whether the foot organ reflex zones and the foot part reflex zones satisfy the theoretical position relationship, the method further comprises:
determining a first sub-zone orientation relationship of the first group of organ reflex sub-zones, a second sub-zone orientation relationship of the second group of organ reflex sub-zones, a third sub-zone orientation relationship of the third group of organ reflex sub-zones, a fourth sub-zone orientation relationship of the fourth group of organ reflex sub-zones, a fifth sub-zone orientation relationship of the fifth group of organ reflex sub-zones, and a sixth sub-zone orientation relationship of the sixth group of organ reflex sub-zones;

judging whether the first sub-zone orientation relationship, the second sub-zone orientation relationship, the third sub-zone orientation relationship, the fourth sub-zone orientation relationship, the fifth sub-zone orientation relationship, and the sixth sub-zone orientation relationship satisfy a theoretical organ orientation relationship;

judging whether the foot organ reflex zones and the foot part reflex zones satisfy the theoretical position relationship specifically is:

when the first sub-zone orientation relationship, the second sub-zone orientation relationship, the third sub-zone orientation relationship, the fourth sub-zone orientation relationship, the fifth sub-zone orientation relationship, and the sixth sub-zone orientation relationship satisfy the theoretical organ orientation relationship, judging whether the foot organ reflex zones and the foot part reflex zones satisfy the theoretical position relationship.

2. The foot reflex zones identification method of claim 1, wherein judging whether the foot organ reflex zones and the foot part reflex zones satisfy the theoretical position relationship, comprises:

determining a first region coordinate range of each of the foot part reflex zones in a preset coordinate system and a second region coordinate range of each of the foot organ reflex zones in the preset coordinate system;

determining an actual position relationship between the foot organ reflex zones and the foot part reflex zones based on the first region coordinate range and the second region coordinate range;

when the actual position relationship matches the theoretical position relationship, the foot organ reflex zones and the foot part reflex zones satisfy the theoretical position relationship.

3. The foot reflex zones identification method of claim 1, wherein judging whether the foot organ reflex zones and the foot part reflex zones satisfy the theoretical position relationship, comprises:

judging whether the first group of organ reflex sub-zones and the head reflex zone, the second group of organ reflex sub-zones and the neck reflex zone, the third group of organ reflex sub-zones and the shoulder-back reflex zone, the fourth group of organ reflex sub-zones and the chest reflex zone, the fifth group of organ reflex sub-zones and the abdominal reflex zone, and the sixth group of organ reflex sub-zones and the genital reflex zone satisfy the theoretical position relationship.

4. The foot reflex zones identification method of claim 1, wherein before judging whether the foot organ reflex zones and the foot part reflex zones satisfy the theoretical position relationship, the method further comprises:

obtaining a theoretical part orientation relationship and an actual part orientation relationship between the foot part reflex zones;

judging whether the actual part orientation relationship satisfies the theoretical part orientation relationship;

judging whether the foot organ reflex zones and the foot part reflex zones satisfy the theoretical position relationship is:

when the actual part orientation relationship satisfies the theoretical part orientation relationship, judging whether the foot organ reflex zones and the foot part reflex zones satisfy the theoretical position relationship.

5. The foot reflex zones identification method of claim 3, wherein the first group of organ reflex sub-zones includes a brain reflex sub-zone, a nose reflex sub-zone, an oral cavity reflex sub-zone, an eye reflex sub-zone, an ear reflex sub-zone, and a frontal sinus reflex sub-zone; the second group of organ reflex sub-zones includes an esophagus-trachea reflex sub-zone, a neck reflex sub-zone, a thyroid reflex sub-zone, and a parathyroid reflex sub-zone; the third group of organ reflex sub-zones includes a trapezius muscle reflex sub-zone and a shoulder reflex sub-zone; the fourth group of organ reflex sub-zones includes a bronchus reflex sub-zone and a lung reflex sub-zone; the fifth group of organ reflex sub-zones includes a liver reflex sub-zone, a kidney reflex sub-zone, a stomach reflex sub-zone, a duodenum reflex sub-zone, a transverse colon reflex sub-zone, an ascending colon reflex sub-zone, a small intestine reflex sub-zone, and a bladder reflex sub-zone; the sixth group of organ reflex sub-zones includes a pelvic region reflex sub-zone, a buttocks reflex sub-zone, and a gonad reflex sub-zone.

6. The foot reflex zones identification method of claim 1, wherein the multi-task deep learning network model includes a shared backbone sub-model, and a parallel organ reflex zone detection head and a part reflex zone detection head, where the step of inputting the foot image into the multi-task deep learning network model to obtain foot part reflex zones and foot organ reflex zones comprises:

obtaining shared image features based on the shared backbone sub-model, the shared backbone sub-model used for feature extraction of the foot image;

obtaining the foot organ reflex zones based on the organ reflex zone detection head, the organ reflex zone detection head used for key point detection of the shared image features;

obtaining the foot part reflex zones based on the part reflex zone detection head, the part reflex zone detection head used for semantic segmentation of the shared image features.

* * * * *